United States Patent
Samolyk

(10) Patent No.: US 6,398,751 B1
(45) Date of Patent: Jun. 4, 2002

(54) CARDIOPULMONARY BYPASS BLOOD RECOVERY METHOD

(76) Inventor: Keith Samolyk, 998 Windsor Ave., Windsor, CT (US) 06095

( * ) Notice: Subject to any disclaimer, the term of this patent is extended or adjusted under 35 U.S.C. 154(b) by 0 days.

(21) Appl. No.: 09/189,230

(22) Filed: Nov. 11, 1998

Related U.S. Application Data

(62) Division of application No. 08/719,971, filed on Sep. 24, 1996, now Pat. No. 5,928,178.

(51) Int. Cl.⁷ .......................... A61M 37/00; A61B 19/00
(52) U.S. Cl. ..................... 604/6.01; 604/5.01; 604/408; 128/DIG. 3
(58) Field of Search ................................. 604/4–6, 403, 604/408, 409, 7, 404, 411, 416; 210/638, 639, 646, 647, 650, 749, 765, 767; 435/2; 436/177, 178; 206/219, 216, 569, 438 AB, 459.1, 459.5, 828; 128/DIG. 3, DIG. 24; 73/53.01, 61.43, 61.63

(56) References Cited

U.S. PATENT DOCUMENTS

| 4,863,452 A | * | 9/1989 | Irmiter et al. ................. 604/408 |
| 4,904,234 A | * | 2/1990 | Shimomura et al. |
| 5,286,388 A | * | 2/1994 | Ingram ......................... 210/560 |
| 5,306,269 A | * | 4/1994 | Lewis et al. ................. 604/403 |
| 5,540,841 A | * | 7/1996 | Gsell et al. .................. 210/645 |
| 5,609,571 A | * | 3/1997 | Buckberg et al. ............... 604/4 |
| 5,634,893 A | * | 6/1997 | Rishton ........................... 604/4 |
| 5,725,492 A | * | 3/1998 | Igo et al. ........................ 604/4 |
| 5,858,238 A | * | 1/1999 | McRea et al. |
| 5,916,191 A | * | 6/1999 | Plunkett et al. ................. 604/4 |
| 5,928,178 A | * | 7/1999 | Samolyk ......................... 604/4 |
| 5,957,137 A | * | 9/1999 | Dalke et al. ................. 128/898 |

* cited by examiner

Primary Examiner—Angela D. Sykes
Assistant Examiner—Patricia M Bianco
(74) Attorney, Agent, or Firm—Alix, Yale & Ristas, LLP

(57) ABSTRACT

A method and blood bag, whereby a substantial volume of concentrated whole blood can be quickly and easily recovered from the cardiopulmonary bypass (CPB) circuit of a patient immediately following cardiac or thoracic vascular surgery. This is achieved in an operating room, by transferring most of the blood in the CPB circuit into a sterile bag located in the surgical field, removing the bag with blood from the surgical field, and outside the surgical field, but preferably in the operating room, hemo-concentrating the blood in the bag, while the bag is fluidly connected to the bypass system hardware. A novel blood bag (or hemo-bag) system is especially adapted for use with the method of the present invention. The new hemo-bag system comprises a closed, sterile bag of substantially transparent, biocompatible material, defining upper and lower ends. An infusion port is located at the upper end of the bag. An outlet port, an inlet port, and an IV line are situated at the lower end of the bag. A baffle is preferably located inside the bag, for directing upward flow entering the bag through the inlet port, away from the outlet port. Each of the ports and line terminate in connector structure, and can be opened or closed by way of conventional clips and caps.

13 Claims, 5 Drawing Sheets

CARDIOPULMONARY BYPASS BLOOD RECOVERY METHOD

This is a divisional of application Ser. No. 08/719,971 filed Sep. 24, 1996 now U.S. Pat. No. 5,928,178.

BACKGROUND OF THE INVENTION

The present invention relates to medical equipment, techniques and procedures, and more particularly, to the circulation and recovery of blood during and immediately following heart bypass surgery.

A persistent dilemma is faced hundreds of times each day worldwide, of how to handle the volume of a patient's blood in the circuit of a cardiac pulmonary bypass system (heart-lung machine), after the surgical procedure has been completed and the patient is disconnected from the bypass system.

One option is to transfuse the volume in the cardiopulmonary bypass (CPB) circuit to the patient, in the manner of a blood transfusion, without compromising the integrity of the bypass system. It should be appreciated that the CPB circuit includes a crystalloid priming fluid which is necessary to initiate the pumping of the circuit. Therefore, transfusion of the content of the circuit would include transfusion of the priming solution which, by the end of the surgery, has been fully mi,(ed with the patient's own blood. The hematocrit concentration is therefore low, i.e., approximately 18–23%. Although some such diluted blood can be transfused to the patient, a relatively large fraction of the volume of the CPB circuit cannot be transfused, because this volume is needed to maintain the integrity of the circuit in the event full bypass is to be resumed.

Alternatively, the content of the CPB circuit can be transferred to sterile blood bags, for a possible re-transfusion to the patient either in or out of the operating room. This option also suffers from the dilution of important blood components and the need to keep a large fraction of the diluted blood in the circuit to maintain circuit integrity.

Yet a third option, is to chase all the volume in the CPB circuit with a crystalloid solution to a so-called "cell saver", where the fluid volume is separated into red blood cells and effluent. Although the red blood cells are saved, the effluent is deemed waste and therefore discarded, yet the effluent contains many desirable constituents of whole blood, such as plasma, platelets, clotting factors, etc.

Finally, the most straight-forward option is to seal or drain and discard the content of the CPB circuit. This is common in pediatric open heart cases, but benefits neither the patient nor anyone else, and presents a significant disposal problem to the perfusionist (i.e., the operator of the heart/lung machine), who must clean up and discard this wasted volume.

Because in the foregoing options, the patient cannot receive his own entire blood volume from the CPB circuit immediately following cardiac or thoracic vascular procedures, if the need for additional blood arises, the only available source is from previously stored blood bags. If the patient gave blood prior to surgery, which is rare, then the patient could receive so-called autologous blood. Most often, however, such additional blood or blood products would be provided from a dwindling blood bank supply, which originated from an allogenic (unknown) donor. Transfusing such blood can arouse anxiety and create problems including hemolytic reactions, viral hepatitis-C, and potentially, blood viruses or AIDS. Human error can occur when mistakes are made by giving non-compatible or mislabelled blood products. Lastly, there is also a small population of patients that completely refuse any foreign blood or blood products of any kind, due for example, to religious beliefs.

Because of these reasons, the need exists to reduce allogenic blood use and strive for "bloodless surgery".

SUMMARY OF THE INVENTION

It is an object of the present invention to provide a method and blood bag, whereby a substantial volume of concentrated whole blood can be quickly and easily recovered from the CPB circuit of a patient immediately following cardiac or thoracic vascular surgery.

It is a further object of the invention, that such recovered blood be available in the operating room for rapid volume replacement and stability of the patient.

It is yet another object of the invention, that the blood be recovered from the CPB circuit while ensuring that the cardiopulmonary bypass circuit remains de-aired and ready for immediate reuse in the event cardiopulmonary bypass assistance for the patient must be resumed.

It is still another object of the invention to provide a bag system for receiving the patient's blood in the field of surgery, and concentrating the blood outside the field for storage in the bag, which can be conveniently handled in or outside the operating room for transfusion to the patient either in or outside the operating room.

These and other objects can be achieved in an operating room, by transferring most of the blood in the CPB circuit into a sterile bag located in the surgical field, removing the bag with blood from the surgical field, and outside the surgical field, but preferably in the operating room, hemoconcentrating the blood in the bag, while the bag is fluidly connected to the bypass system hardware.

The inventive method according to the invention, can also be considered as including the steps after the bypass system connections have been removed from the patient, of first, fluidly connecting the CPB circuit outlet e.g., arterial line, downstream of the arterial pump to a sterile blood bag. The blood in the CPB circuit is then chased into the blood bag with, e.g., crystalloid solution. The blood bag is fluidly connected to a closed hemoconcentration circuit, and when the hematocrit concentration of the blood in the bag reaches a desired value, the bag is sealed, labelled, and made available for transfusion to the patient either in or out of the operating room.

A novel blood bag (or hemo-bag) system is especially adapted for use with the method of the present invention. The new hemo-bag system comprises a closed, sterile bag of substantially transparent, bio-compatible material, defining upper and lower ends. An infusion port is located at the upper end of the bag. An outlet port, an inlet port, and an IV line are situated at the lower end of the bag. A baffle is preferably located inside the bag, for directing upward flow entering the s bag through the inlet port, away from the outlet port. Each of the ports and line terminate in connector structure, and can be opened or closed by way of conventional clips and caps.

The preferred method according to the invention is implemented after cardiopulmonary bypass has ceased, and the cannulas connected to the CPB circuit have been removed from the patient. The venous line of the CPB circuit can be drained backward with crystalloid solution, from a bucket on the field, and then clamped, keeping the venous line intact with priming fluid, for use in the event a restart of the bypass system for the patient, becomes necessary. The arterial line cannula is removed from the patient and circuit, and the arterial line is connected to the infusion port at the top of the hemo-bag, while all the clips on the ports and lines at the bottom of the hemo-bag are closed and capped. Volume from the CPB circuit is then chased with crystalloid solution through the CPB circuit, filling the hemo-bag with the patient's blood from the circuit. Both the arterial line and the infusion port at the top of the hemo-bag are then clamped. An appropriately sized connector with a Luer can be placed between the venous and arterial lines and fluid recirculated so the CPB circuit remains intact (i.e., with enough priming fluid to resume pumping without ingress of air), thereby protecting its integrity for reinstitution of bypass if necessary. Once the dead end cap is on the infusion port the hemo-bag becomes a sterile closed container of the patient's blood which can be handed off the field of surgery, to the perfusionist, outside the field of surgery.

The perfusionist then connects the hemo-bag to a hemo-concentrator, such that the blood from the outlet port at the bottom of the hemo-bag flows into the hemo-concentrator and the concentrated blood flow from the hemo-concentrator enters the inlet port at the bottom of the bag. Typically, a spare roller pump in the console of the cardiopulmonary bypass system is used to actively circulate the blood, in this hemo-concentration circuit.

Once the concentration reaches a satisfactory level, the outlet port of the hemo-bag is clamped off and, preferably, the blood in the recirculation circuit is chased into the bag as the pump operates, by allowing air through, for example, a Luer port near the closed outlet port of the bag. Once air enters the hemo-bag, the pump is stopped, the bag inlet port is then clamped off, the hemo-concentrator is disconnected, and the caps on the bottom are reclosed. The hemo-bag is labelled for the patient and handed up to the anesthesiologist at the head of the patient, where, if necessary, the IV line can be spiked and the hemo-concentrated whole blood can be infused in a timely manner. This benefits the patient by saving time, money, and in many cases, eliminating the need for and anxiety associated with, allogenic blood bank products. Alternatively, the hemo-bag can be easily transported for later transfusion into the patient, as necessary after the patient has been removed from the operating room.

BRIEF DESCRIPTION OF THE DRAWINGS

These and other objects and advantages of the invention will be evident to practitioners in this field, upon reading the following description of the preferred embodiment in conjunction with the accompanying drawing, in which.

DESCRIPTION OF THE PREFERRED EMBODIMENT

Figure 1:
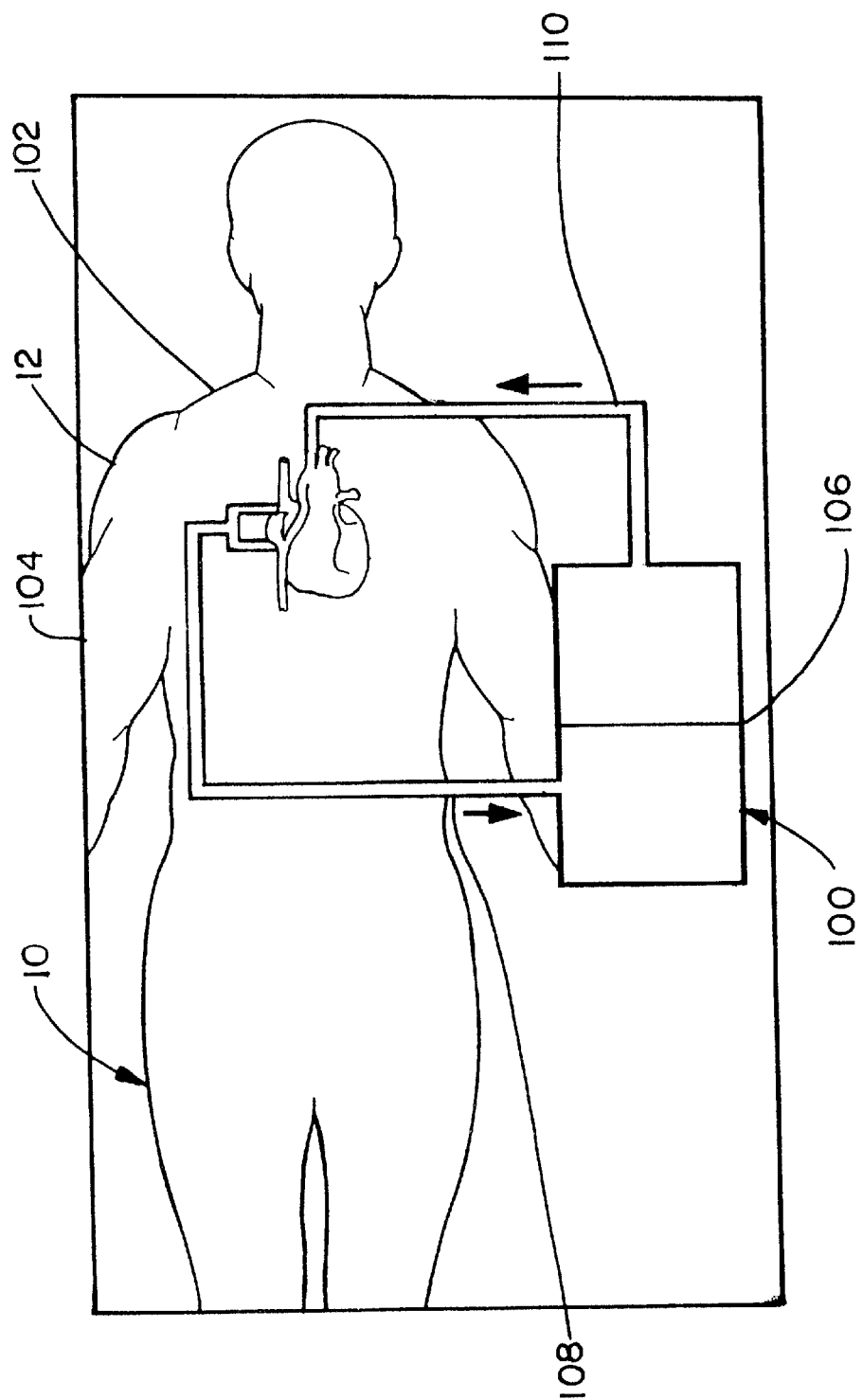
FIG. 1 is a schematic representation of a cardiopulmonary bypass system connected to a patient during surgery.

FIG.1 schematically shows a patient 10 during heart bypass surgery, wherein a cardiopulmonary bypass (CPB) system, also known as a heart/lung machine 100, is connected to the patient's heart 12. The CPB system 100 includes an arterial cannula 102 inserted into the ascending aorta at the heart 12 and a venous cannula 104 inserted into one or both of the vena cava. Arterial pump 106 (and associated components to be described hereinafter), receives deoxygenated blood from the venous cannula 104, via inlet line 108, and delivers externally oxygenated blood via outline line 110, to the arterial cannula 102.

Figure 2:
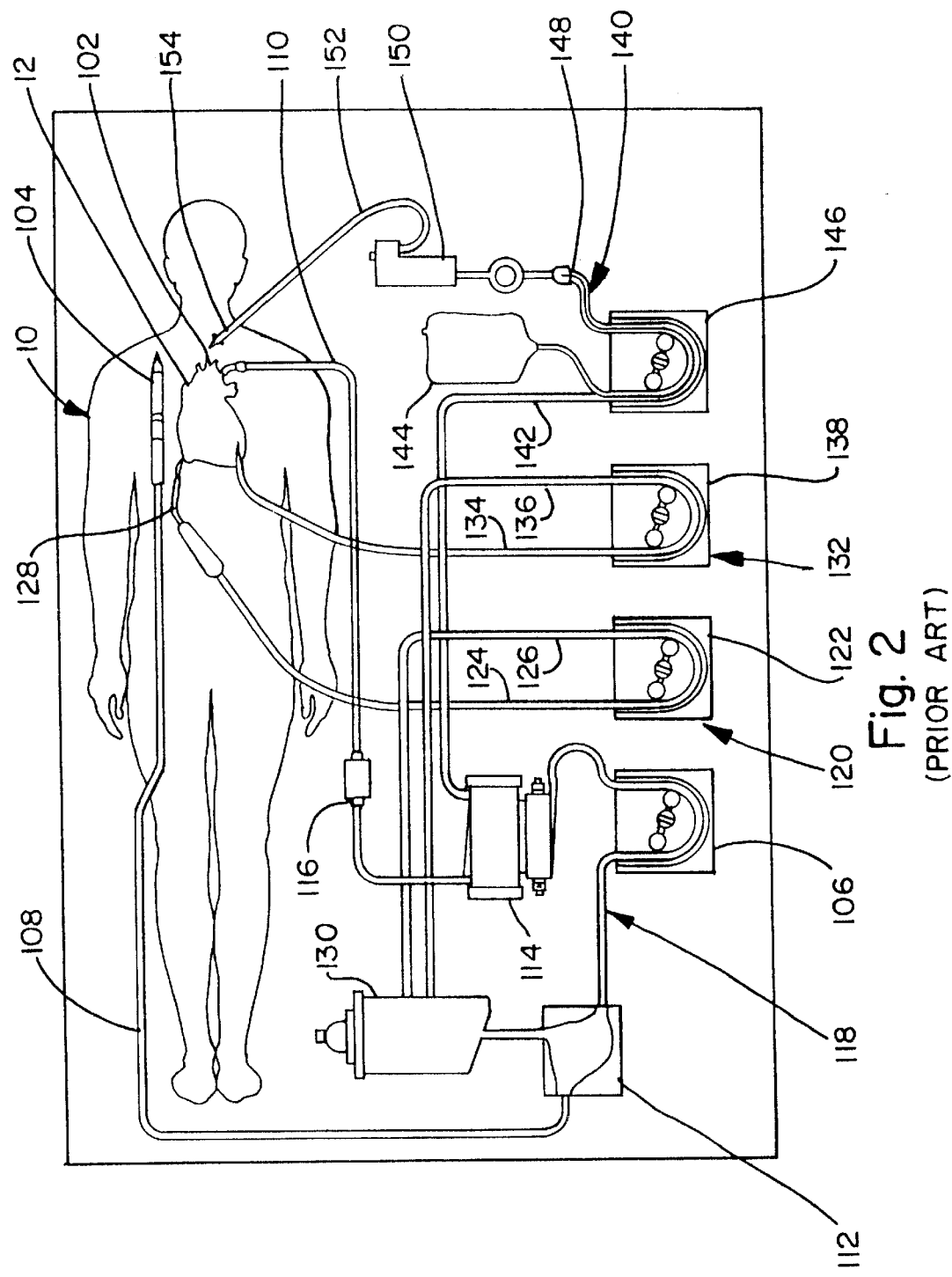
FIG. 2 is a schematic representation of the bypass system, showing various fluid circuits as connected during surgery.

FIG. 2 shows additional details represented schematically, of one conventional arrangement by which the CPB system 100 is connected to the patient 10 during bypass surgery. Deoxygenated blood in the inlet line 108 enters a venous reservoir 112, which is fluidly connected to the arterial pump 106. The discharge from the pump 106 enters a heat exchanger and oxygenator 114, passes through an arterial filter 116, before eventually entering the arterial cannula 102. The components and lines 102–116, can be considered collectively, as defining a CPB circuit 118.

The CPB system 100 typically includes other circuits as well. A field suction circuit 120 includes a roller pump 122, a suction inlet line 124 to the pump 122, and a suction outlet line 126 which returns to the venous reservoir 112 (or optionally a cardiotomy reservoir 130 prior to the venous reservoir). The suction inlet 124 terminates in a so-called "field sucker" 128, by which bleeding at the field can be recovered during surgery.

Another circuit is the vent circuit 132, having a vent inlet line 134 leading to a roller pump 138, from which air and blood vented from the heart 12, can eventually be delivered via outlet line 136 to the venous reservoir 112 or cardiotomy reservoir 130.

A cardioplegia circuit 140 is typically present, whereby sometimes oxygenated blood can be drawn from the oxygenator 114, via cardioplegia inlet line 142, into the cardioplegia pump 146, where cardioplegia solution from bag 144 can be mixed therewith, for delivery via cardioplegia outlet 148, to a cardioplegia processing unit 150. The processing unit 150 typically includes a heat exchanger, a bubble trap, and temperature and pressure monitor. The outlet line 152 from the unit 150, terminates in a cardioplegia cannula 154.

Those familiar with surgery understand that when the patient and the CPB system 100 represented in FIG. 2, are situated in the operating room, a pre-defined space immediately surrounding and extending upwardly from the patient 10, is referred to as the "field" of surgery, which is subject to extra precautionary procedures and access. The surgeon and surgical assistants perform the operation in the field, with support from several specially trained nurses and assistants. The perfusionist operates the CPB system 10, outside the field of surgery. Only the surgeon and surgical assistants, can place and manipulate the cannulas and other terminal end effectors of the various CPB circuits, within the field of surgery.

Figure 3:
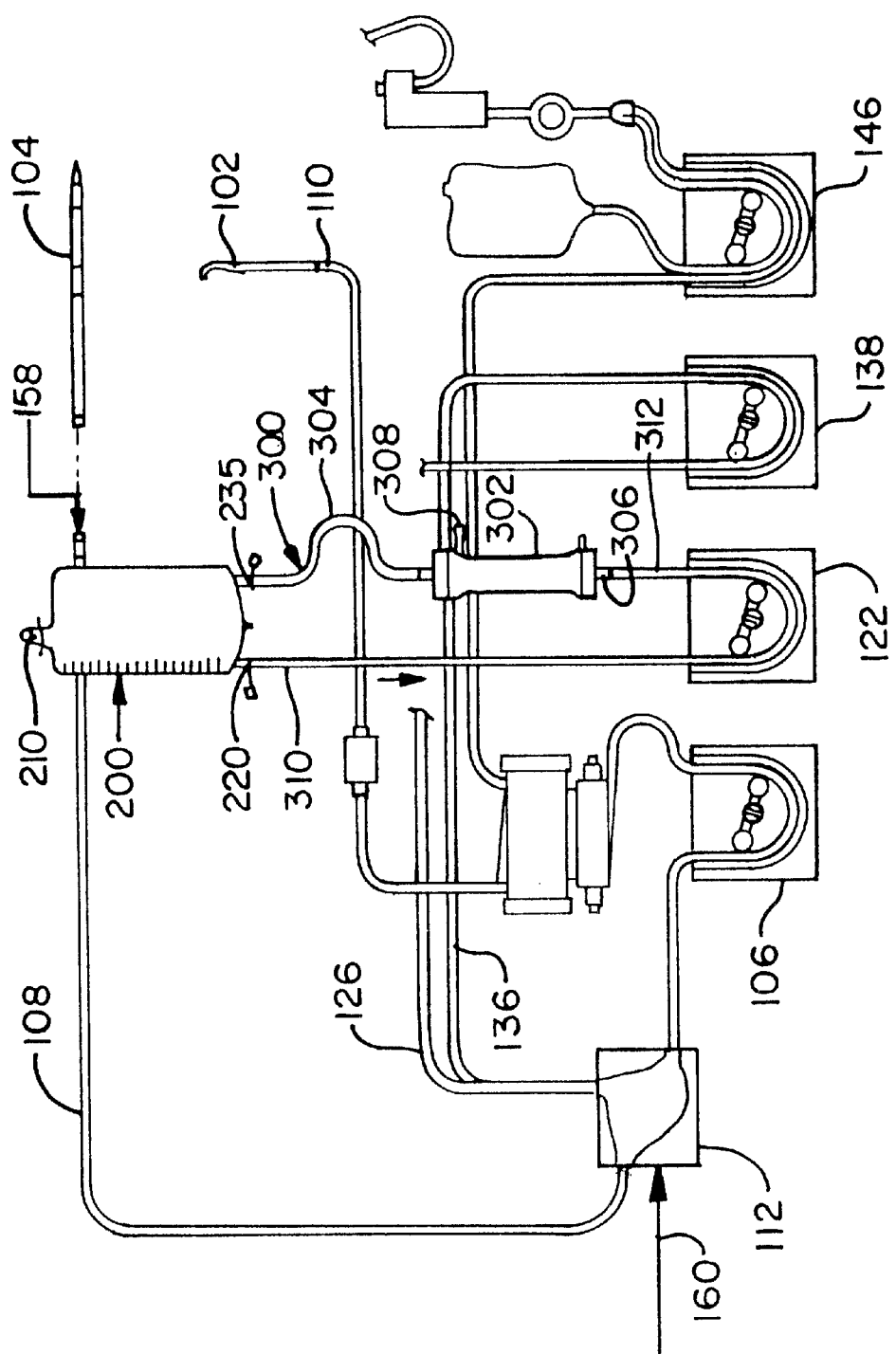
FIG. 3 is a schematic representation of how the circuits shown in FIG. 2 can be modified during a particular step of the method according to the present invention.
Figure 4:
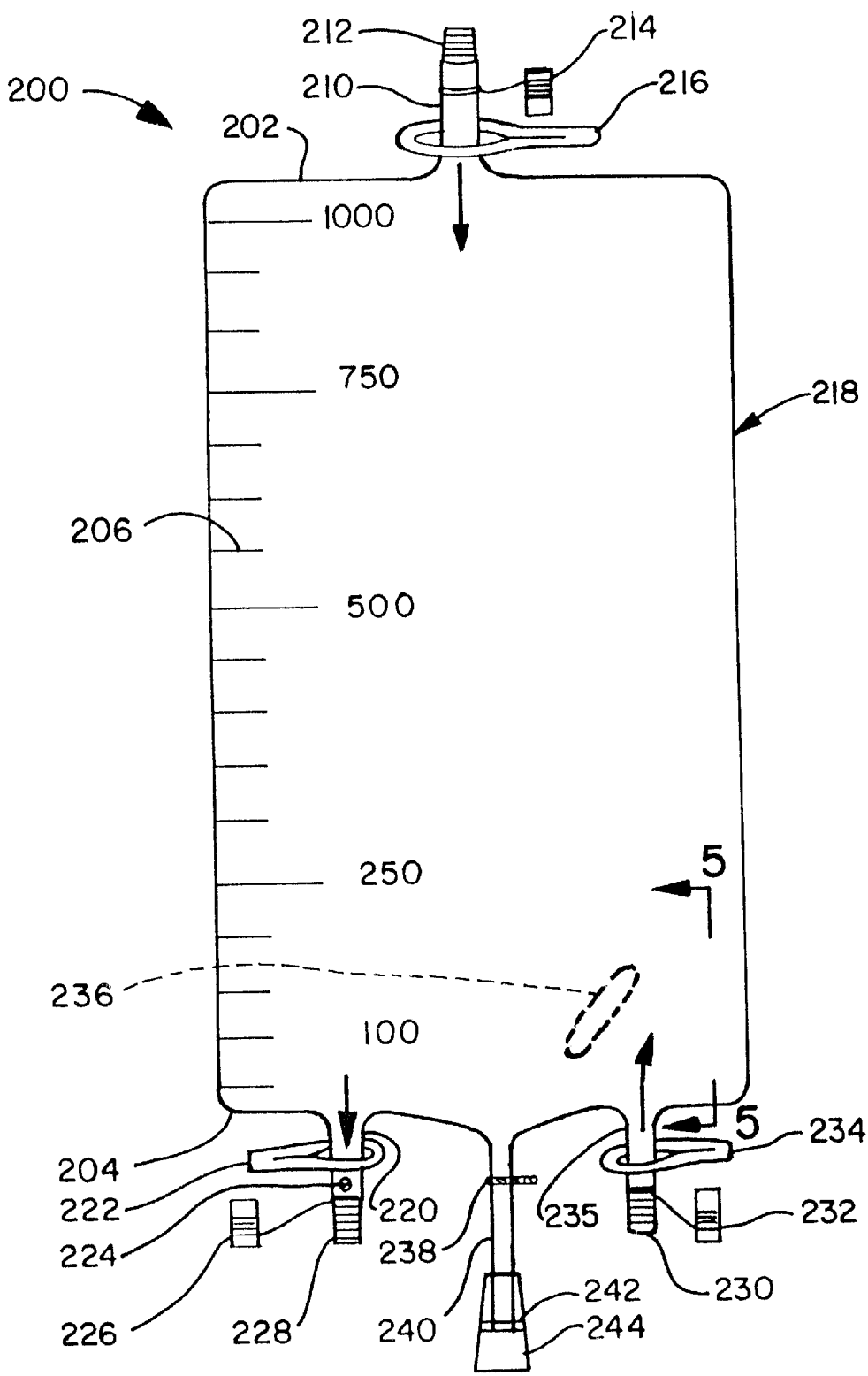
FIG. 4 is an elevation view of the hemo-bag shown in FIG. 3, according to the preferred embodiment.

With reference now to FIGS. 3 and 4, the preferred embodiment of the invention will be described in detail. A specially adapted hemo-bag 200 of appropriate size such as shown in FIG. 4, is selected by a surgical assistant who in the field, will transfer most of the blood in the CPB circuit 118, into the bag 200. The bag 200 with blood, is sealed and removed from the surgical field and, outside the surgical field, the bag is connected to a hemo-concentrating circuit 300, as shown in FIG. 3.

The bag 200 as shown in FIG. 4, is in effect a bag system, comprising a closed, sterile bag 218 of substantially transparent, bio-compatible material, of a type conventionally used for blood storage/and or transfusion, e.g., polyvinyl. Such bags are typically oblong, thereby defining upper (top) and lower (bottom) ends 202,204. The front side of the bag is marked with a scale 206, indicating the volummetric gradations of the content of the bag. Typical bag sizes are 750, 1000 or 1500 milliliter.

An arterial infusion port 210 is situated at the top of the bag, and serves as the conduit for entry of blood from the arterial line 110 of the CPB circuit 118 after the cannulas 102,104 have been removed from the patient. The conduit defining the infusion port 210, terminates in preferably, a stepped and tapered ¼–⅜ inch universal arterial infusion connector 212. A dead end cap with a leash 214 and a clip 216 are carried by the conduit, and function therewith in a conventional manner. The clip 216 is preferably a so-called master clip, which can also serve as a hanger for the hemo-bag, after it has been filled with blood.

At the lower end 204 of the bag 218, an outlet port 220 is defined by preferably, a ¼ inch conduit on which a clip 222 is carried. Preferably, a ¼ inch Luer connector 224 is connected to the conduit 220, or formed integral therewith, for selectively admitting a flow of air or fluid bidirectionally for reasons to be discussed more fully below. A ¼ inch connection 228 extends below the Luer 224, and a dead end cap with leash 226 is carried thereon.

An inlet port 235 is also situated in spaced relation from the outlet port 220, at the bottom or lower end of the bag. The inlet port is typically defined by a conduit having a ¼ inch end connector 230, which carries a dead end cap with leash 232. A clip 234 is carried by the inlet conduit 235.

An intravenous IV line 240 is also situated at the lower end of the bag. This is a conventional IV line, having a clip 238 and a terminal female connector 242 for receiving a male IV spike when the contents of the bag are to be transfused to the patient. The IV line 240 is preferably situated between the outlet port 220 and the inlet port 235 and has a sterile cap 244.

Referring to FIGS. 3 and 4, when the bag 200 as depicted in FIG. 4, is handed to field personnel, the inlet clip 222 and cap 226, outlet clip 234 and cap 232, and IV clip 238 and cap 244 are placed in the closed condition, whereas the infusion clip 216 and cap 214 are open. In the field, the arterial cannula 102 is removed from line 110, which is typically a ¼ or ⅜ inch line, and the line is then secured to the universal connector 212 at the infusion port 210 of the bag. The venous cannula 104 is detached from line 108, and a crystalloid solution, is introduced as shown at 158, into line 108. This chases the blood in the CPB circuit 118, along line 108, through the venous reservoir 112, the pump 106 and the remaining components, whereby most of the patient's blood in the CPB circuit 18, is chased into the hemo-bag 200. As an alternative, crystalloid solution can be introduced at the venous reservoir 112, via line 160, as a more convenient way of chasing most, but not all, of the blood in the CPB circuit 118 into the bag 200.

When the bag 200 has been filled in the field according to the manner described above, the field personnel closes the infusion port 210 using the clip 216 and cap 214 and reconnects the arterial and 10 venous lines with the appropriate size Luer connector for recirculation.

The filled bag is then handed to personnel outside the field, typically the perfusionist, who will then establish the hemo-concentrating circuit 300 as depicted in FIG. 3. The bag can be hung in any convenient manner, via the master clip 216. There are a variety of available circuits of the CPB system 100, other than the arterial circuit 118, which can be disconnected and reconfigured to form the hemo-concentration circuit 300. When available, however, connections are made to a spare roller pump. In the example shown in FIG. 3, the suction circuit 120 of FIG. 2, has been removed from roller pump 122. A new ¼ inch line is connected through the pump 122 from the outlet port 220 of the hemo-bag via line portion 310, and line portion 312 is connected between the outlet of the pump 122 and the inlet 306 of a hemo-concentrator 302. The outlet of the concentrator 302 is attached via new line 304, to the inlet port 235 of the bag. The hemo-concentrator 302 can be of any conventional configuration, e.g., such as is available as Model HPH1000TS from the Mintech Corporation, Minneapolis, Minn. In such hemo-concentrators, a flow of effluent is discharged at 303. The effluent at 308 is removed and only the hematocrit- enriched blood is delivered through line 304 to the bag 200.

Alternatively, a circuit such as 120 of FIG. 2 can be reconfigured by removing the sucker 128 from inlet line portion 124, disconnecting outlet line portion 126, and then reconnecting line portion 124 to the outlet port 220 of the hemo-bag and line portion 126 to the inlet 306 of the hemo concentrator 302.

In the configuration shown in FIGS. 3 and 4, clip 222 on the bag 200 is opened, thereby permitting a blood flow down line 310 into the pump 122. The inlet port 235 is opened via movement of clip 234, and the pump 122 is started, to establish a circulatory flow in the hemo-concentration circuit 300.

Figure 5:
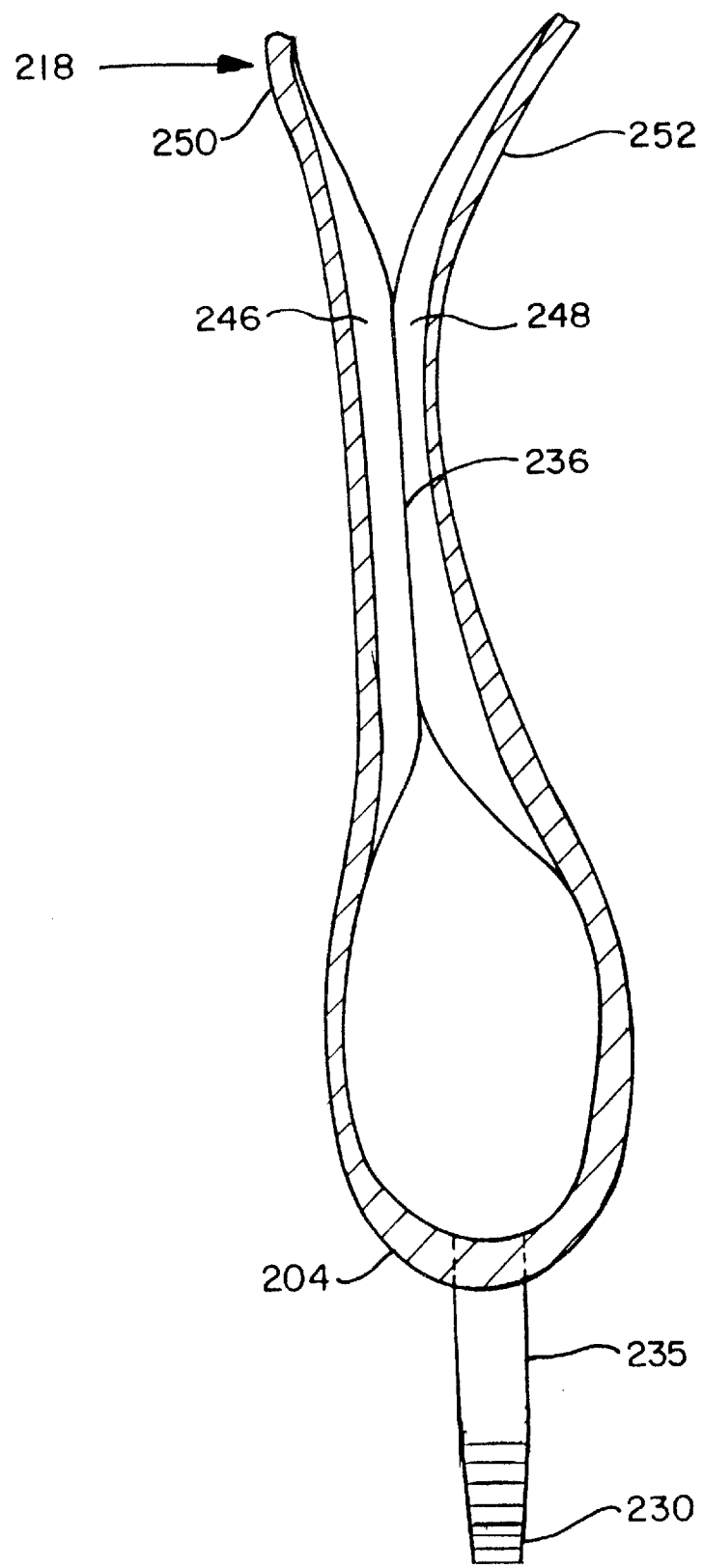
FIG. 5 is a section view of the baffle in the hemo-bag, taken along line 5—5 of FIG. 4.

With reference again to FIG. 4, the hemo-bag 200 preferably includes a baffle 236 located inside the bag, and oriented for directing upward flow entering the bag through the inlet port 235, away from the outlet port 220. The baffle 236 assures even mixing of blood which has been received from the hemo-concentrator 302, with the less concentrated blood in the bag. In particular, the baffle 236 is located closer to the inlet port 235 than to the IV line 240 thereby blocking lateral flow of the concentrated blood when it enters the bag. FIG. 5 shows the baffle 236 as formed by pinching and heat sealing together, portions 246,248 of the front 250 and back 252 walls of the bag 218.

Alternatively, a distinct, oblong member (not shown) could be fixed between the walls, preferably at an angle to the vertical.

When the blood in the hemo-concentration circuit 300 reaches an appropriate concentration of hematocrit (for example, as represented by the percent volume reduction from the time circulation in configuration 300 was initiated), the roller pump 122 is stopped and outlet port 220 is closed via clip 222. A flow of air is introduced through Luer 224, which is below the clip 222, such that the fluid in line 310, pump 122, hemo-concentrator 302, and line 304 is deprimed and chased back into the bag 200, by pumping through inlet port 235, and the pump 122 is turned off. The clip 234 then closes port 235, and lines 125 and 304 are disconnected from the end connectors 228 and 230. At this point, all clips 216,222 and 234 are closed, and the respective dead end drip caps 214,226 and :232 can be secured to the respective end connectors 212,228 and 230. Line 240 has remained closed by clip 238, and sterile by cap 244.

It should be appreciated that a key feature of the invention, is that the hemo-bag 200 is filled in the field, and the closed bag with blood from the CPB circuit 118 is handed outside the field, where hemo-concentration occurs. Although it is preferable that hemo-concentration occur in the operating room adjacent to the field, without undermining the integrity of the CPB circuit, this is not absolutely necessary. For example, the bag can be taken out of the operating room, and hemo-concentration achieved at a different time and different place. Nevertheless, it is contemplated that in most operating rooms, the, hemo-concentration will be completed and the hemo-bag with concentrated blood will be available for transfusion, during the time period when the patient is in the operating room. Although the lines 108 and 110 as shown in FIG. 3 have been disconnected from the patient, these lines are clamped immediately after the bag 200 has been filled. The CPB circuit 118 thus is filled with crystalloid solution, and need not be re-primed in the event reestablishment of the CPB circuit is necessary. In this eventuality, the patient's own concentrated blood is readily available from the hemo-bag 200, merely by spiking with a standardized connection at IV port 242.

It should also be appreciated that variations of the invention other than those specifically described herein, can fall within the scope of the appended claims. For example, a typical CPB system 100 may have five or more pumps therein, such that establishment of the hemo-concentration circuit 300 can be made with a pump that was not in use during the actual surgical procedure. Furthermore, a pump from a circuit other than the suction circuit, could be used for establishing the hemo-concentration circuit. If a hemo concentrator is already in use during surgery, a "Y" junction can be placed at the top and bottom of the hemo-concentrator so that hemo concentration can take place during and after bypass by means of the hemo-bag. In another variation, after the hemo bag has been disconnected from the arterial line, an appropriately sized connector with a Luer can be used to connect the arterial and venous lines for added safety and recirculation The hemo-bag system 200 according to the invention, could also vary from that described herein. The inventive hemo-bag could be manufactured and sold to a hospital, without the connectors 212,228,230 or other end-effectors. Such bag would merely have port tubing ends available for insertion of end effectors, by the purchaser of the bag. Furthermore, the designation of "top" and "bottom" or "upper" and "lower" ends of the bag as set forth above, should be understood in the context of the functionality of the various ports and IV line. Therefore, the upper end or top 202 of the bag 218 refers to a location at which blood enters to substantially fill the bag, and the lower end or bottom 204, refers to locations where on the one hand, substantially all the content of the bag can be drained by gravity, or on the other hand, where the relative location of the inlet port 235 and the outlet port 220, will assure reasonably thorough mixing of the content of the bag, during flow therebetween. The equivalent functionality, may be achieved by a different geometric relationship between the ports, with or without a baffle. Although not preferred, the infusion port 212 can be used as a substitution for one of the inlet or outlet ports 220,235. Thus, in the hemo-bag system embodiment of the invention, at least two spaced apart ports 210,235 and 220 with associated conduits are necessary, for filling the bag and accommodating recirculation flow as part of the hemo-concentration circuit. A separate IV line 240 is normally present, for the eventual transfusion of the blood to a patient, but the Luer 224 in the outlet port conduit 220 could be used for transfusion as a substitute for or in addition to the IV line 240.

What is claimed is:

1. In an operating room where a cardiopulmonary bypass (CPB) system is used on a patient in a surgical field to introduce externally oxygenated blood into the patient through an arterial cannula and to remove deoxygenated blood from the patient through a venous cannula, by means of a CPB circuit, a method of recapturing the patient's blood from the CPB circuit after the arterial cannula and venous cannula have been removed from the patient, comprising:

(a) transferring at least most of the blood in the CPB circuit into a sterile bag located in the surgical field;

(b) removing the bag with blood from the surgical field;

(c) outside the surgical field, hemo-concentrating the blood in the bag;

(d) sealing the bag containing hemo-concentrated blood;

(e) removing the sealed bag from the operating room;

(f) removing said patient from the operating room; and (g) after step (f), transfusing blood from said sealed bag to said patient.

2. The method of claim 1, wherein step (c) is performed while the bag is fluidly connected to the bypass system.

3. The method of claim 2, wherein step (c) includes connecting flow lines between the bag and a hemo-concentrator and between said hemo-concentrator and the CPB circuit, and then recirculating the blood in the bag through said hemo-concentrator.

4. The method of claim 1, wherein step (c) is performed in the operating room by a perfusionist.

5. In an operating room where a cardiopulmonary bypass system (CPB) is used on a patient to introduce externally oxygenated blood into the patient through an arterial cannula and to remove deoxygenated blood from the patient through a venous cannula, by means of a CPB circuit including an arterial pump having an inlet line fluidly connected to the venous cannula, an outlet line fluidly connected to the arterial cannula, and a venous reservoir interposed between the venous cannula and the arterial pump, the method of operating the system after the arterial cannula and venous cannula have been removed from the patient, comprising:

(a) fluidly connecting the CPB circuit outlet line to a sterile blood bag;

(b) chasing blood in the CPB circuit into the blood bag by displacing blood in the CPB circuit from at least the venous reservoir and the outlet line into the bag, with a crystalloid solution;

(c) fluidly connecting the blood bag to a closed hemo-concentration circuit, and (d) when the hematocrit concentration of the blood in the bag reaches a desired value, closing and removing the bag from the hemo-concentration circuit.

6. The method of claim 5, wherein the step of fluidly connecting the CPB circuit outlet line includes suspending the bag in the field of surgery such that the bag has upper and lower ends, and connecting said outlet line to an infusion portal at the upper end of the bag.

7. The method of claim 6, wherein step (c) is preceded by the step of clamping the infusion port, and step (c) includes fluidly connecting an outlet port at the lower end of the bag to deliver blood from the bag to a hemo-concentrator, and fluidly connecting the hemo-concentrator to an inlet port at the bottom of the bag to receive concentrated blood from the hemo-concentrator.

8. The method of claim 7, wherein in step (d), said closing includes clamping the inlet and outlet ports, and said removing of the bag from the hemo-concentration circuit is preceded by disconnecting the bag from the hemo-concentration circuit and closing the ports with dead end caps.

9. The method of claim 8, wherein in step (d), the outlet port is first clamped, blood in the hemo-concentration circuit is chased with air into the bag, and the inlet port is clamped.

10. The method of claim 6, wherein step (c) is preceded by the steps of clamping the infusion port while the bag is in said field, and passing said clamped bag outside of the field, and steps (c) and (d) are performed outside said field.

11. The method of claim 5, wherein the bypass system includes at least one other circuit having another pump and an inlet line in which fluid is drawn by the other pump, and wherein the step of fluidly connecting the blood bag includes disconnecting said another circuit and fluidly connecting said bag to said another pump and to a hemo-concentrator.

12. The method of claim 5, including the further step (e) of holding the bag with concentrated blood in the operating room and transfusing said concentrated blood to said patient in the operating room.

13. Following a surgical procedure performed on a patient in a surgical fields, wherein the procedure includes circulating the patient's blood outside the body through an extracorporeal circuit including an arterial line with a cannula in the surgical field insertable into the patient for introducing blood, a method of recovering a substantial volume of whole blood from said circuit, comprising:

(a) fluidly connecting a sterile bag to said arterial line in the surgical field and in the surgical field transferring at least most of the blood in said circuit into a the sterile bag;

(b) fluidly disconnecting said bag from the arterial line, removing said bag from the surgical field, and hemoconecentrating the blood in said bag; and (c) transfusing the hemoconcentrated blood from said bag to said patient.

* * * * *

UNITED STATES PATENT AND TRADEMARK OFFICE
CERTIFICATE OF CORRECTION

PATENT NO. : 6,398,751 B1
DATED : June 4, 2002
INVENTOR(S) : Samolyk

It is certified that error appears in the above-identified patent and that said Letters Patent is hereby corrected as shown below:

Column 10,
Line 4, after "surgical", delete "fields" and insert -- field --.
Line 12, after "into", delete "a".

Signed and Sealed this

Fifteenth Day of October, 2002

*Attest:*

*Attesting Officer*

JAMES E. ROGAN
*Director of the United States Patent and Trademark Office*